US009763627B2

(12) United States Patent
Hasegawa et al.

(10) Patent No.: US 9,763,627 B2
(45) Date of Patent: Sep. 19, 2017

(54) ELECTRONIC DEVICE, DISPLAY CONTROL METHOD AND PROGRAM

(71) Applicant: SEIKO INSTRUMENTS INC., Chiba (JP)

(72) Inventors: Takanori Hasegawa, Chiba (JP); Akira Takakura, Chiba (JP); Keisuke Tsubata, Chiba (JP); Kazuhiro Koyama, Chiba (JP)

(73) Assignee: SEIKO INSTRUMENTS INC. (JP)

( * ) Notice: Subject to any disclaimer, the term of this patent is extended or adjusted under 35 U.S.C. 154(b) by 182 days.

(21) Appl. No.: 14/059,546

(22) Filed: Oct. 22, 2013

(65) Prior Publication Data

US 2014/0121567 A1    May 1, 2014

(30) Foreign Application Priority Data

Oct. 25, 2012   (JP) ................. 2012-235943
Aug. 27, 2013   (JP) ................. 2013-176012

(51) Int. Cl.
*A61B 5/024*      (2006.01)
*A61B 5/00*       (2006.01)
*A61B 5/08*       (2006.01)
*G04F 10/00*      (2006.01)
*G04G 21/02*      (2010.01)

(52) U.S. Cl.
CPC ............ *A61B 5/742* (2013.01); *A61B 5/0024* (2013.01); *A61B 5/024* (2013.01); *A61B 5/0816* (2013.01); *A61B 5/4866* (2013.01); *A61B 5/681* (2013.01); *G04F 10/00* (2013.01); *G04G 21/025* (2013.01)

(58) Field of Classification Search
CPC ... A61B 5/024; A61B 5/02438; A61B 5/7445; A61B 5/0402; A61B 5/044; A61B 5/681; A61B 5/742; G04G 21/025
See application file for complete search history.

(56) References Cited

U.S. PATENT DOCUMENTS

| | | | | |
|---|---|---|---|---|
| 5,795,301 A | * | 8/1998 | Yasukawa | A61B 5/02438 482/8 |
| 7,065,006 B2 | * | 6/2006 | Ciervo | G04G 9/0064 368/223 |
| 7,887,492 B1 | | 2/2011 | Rulkov et al. | 600/500 |

(Continued)

OTHER PUBLICATIONS

Oliver, N. et al., "Towards Wearable Physiological Monitoring on a Mobile Phone", pp. 1-28.

*Primary Examiner* — Michael C Stout
*Assistant Examiner* — Nicholas E Kolderman
(74) *Attorney, Agent, or Firm* — Adams & Wilks

(57) ABSTRACT

An electronic device includes a living-body signal receiver that receives a living-body signal, and a display information processor that calculates living-body information based on a living-body signal received by the living-body signal receiver, that measures and outputs internal measurement information, and that determines whether or not the living-body signal receiver receives the living-body signal. A display is configured to display the living-body information and the internal measurement information. A display controller performs a switching operation to switch between the living-body information and the internal measurement information for display on the display based on the result of the determination by the display information processor.

19 Claims, 9 Drawing Sheets

(56) References Cited

U.S. PATENT DOCUMENTS

| | | | |
|---|---|---|---|
| 2006/0079794 A1 | 4/2006 | Liu et al. | 600/502 |
| 2010/0331145 A1* | 12/2010 | Lakovic | G04F 10/00 |
| | | | 482/8 |
| 2012/0253485 A1* | 10/2012 | Weast | G06F 19/3481 |
| | | | 700/91 |
| 2012/0316471 A1* | 12/2012 | Rahman | G06F 1/3296 |
| | | | 600/595 |
| 2013/0106684 A1* | 5/2013 | Weast | G06F 19/3481 |
| | | | 345/156 |

* cited by examiner

ELECTRONIC DEVICE, DISPLAY CONTROL METHOD AND PROGRAM

BACKGROUND OF THE INVENTION

Field of the Invention

The present invention relates to an electronic device, a display control method, and a program.

Background Art

In an electronic device that has a limited display screen, such as a wrist watch, a user needs to switch between display items in order to display desired information. For example, a running watch with a heart rate meter switches between the presence and absence of display of the number of heartbeats depending on a user button operation.

Furthermore, a method in relation to a display switch, disclosed in Japanese Patent No. 04354395, enables or disables a mode function of a multimode type electronic device. The multimode type electronic device includes a mode-selection mode, a visually recognizable mode that has a mode-display body and cooperates with the mode-display body, and at least one hidden mode that has a mode-display body and cooperates with the mode-display body and is switched between display permission and display prohibition. In the mode-selection mode, by switching between the visually-recognizable mode and the hidden mode, the corresponding visually recognizable mode displays the mode-display body thereof. In the hidden mode, conditions are determined such as whether data in the mode-display body of the hidden mode is non-zero or is updated or changed in a recent predetermined period of time. If any one of the conditions is satisfied, the hidden mode is made usable and thus the mode-display body thereof is displayed to be selectable in the switching step. If none of the conditions are satisfied, a state of the display prohibition is maintained, and the hidden mode is skipped.

Accordingly, improved programming and a mode selection method for the multimode (multifunction) type electronic device can be provided, and the user can create a customer specification for himself or herself. As a result, a function of the electronic device, particularly, the watch, can be more specifically formed.

Furthermore, in a portable pulse wave measurement device disclosed in Japanese Patent No. 03468390, a display form of a change in a pulse rate over time in a dot display region is changed between a first measurement period from the start of time measurement until the pulse rate reaches a predetermined designated range and a second measurement period after the pulse rate reaches the predetermined designated range.

Accordingly, for example, if the portable pulse wave measurement device is used for monitoring the pulse rate during a marathon, although the dot display region is small, when occasionally looking at the dot display region of the display device, a runner can simply grasp which level the pulse rate is at depending on which form the display is in.

Furthermore, in a pulse wave measurement device disclosed in Japanese Patent No. 03492044, an original waveform of a pulse wave signal is displayed in a graphic form on the display device until an external operation is performed in such a manner that the measurement of the time is started after switching is made to a measurement mode of pulse form information, based on the external operation.

Accordingly, if the waveform or the level of the original waveform of the pulse wave signal is checked before starting to measure the pulse wave information, it can be determined in detail whether or not an installation state of an element for detecting the pulse wave signal is good or bad.

Occasionally, information that the user desires to view differs depending on the purpose of and the situation of using an electronic device. For example, in a case where the user uses the running watch, it is considered that when using the running watch as a heart rate meter, the user desires to view the number of heartbeats and in contrast, when using the running watch as a stopwatch, the user desires to view a lap time, a split time, or the like.

At this point, if the user performs a switching operation, depending on the information he or she desires to view, the switching operation is a laborious job for himself or herself. For example, if the user performs the switching operation by pushing on a button to display the desired information such as the lap time, the split time, the number of heartbeats, or the like when he or she starts to get or is getting exercise such as running, the switching operation is a laborious job for himself or herself.

With regard to this, in the method disclosed in Japanese Patent No. 04354395, the display of a display mode corresponding to a function not in use is skipped when sequentially switching among the display modes, and a user operation for the display switching is necessary.

Furthermore, in the portable pulse wave measurement device disclosed in Japanese Patent No. 03468390 and the pulse wave measurement device disclosed in Japanese Patent No. 03492044, if it is possible to reduce the user's laborious job of performing the display switching operation, convenience is further increased.

SUMMARY OF THE INVENTION

It is an aspect of the present application to provide an electronic device, a display control method, and a program, all of which are capable of reducing a user's laborious job of performing a display switching operation.

According to the present application, there is provided an electronic device including a display unit that displays information, a living-body signal acquisition unit that acquires a living-body signal indicating a result of measuring living-body information from a measurement device that measures the living-body information, an internal measurement unit that outputs internal measurement information that is measured within the internal measurement unit, and a display control unit that determines whether or not the living-body signal acquisition unit acquires the living-body signal and that performs switching between the internal measurement information output by the internal measurement unit and information relating to the living-body information indicated by the living-body signal for display on the display unit, based on a result of the determination.

The electronic device may further include a determination unit that determines whether or not the living-body signal acquisition unit acquires the living-body signal, in which the display control unit may perform the switching between the internal measurement information output by the internal measurement unit and the information relating to the living-body information indicated by the living-body signal for display on the display unit, based on the result of the determination by the determination unit.

In the electronic device, the internal measurement information may include at least one of a point in time, a time, the number of steps, running acceleration, a distance based on the number of steps, and consumption calorie based on the number of steps.

In the electronic device, the determination unit may perform the determination, based on whether or not the living-body signal is received within a predetermined period of time.

In the electronic device, the determination unit may determine whether or not the living-body signal acquired by the living-body signal acquisition unit falls within a range of a predetermined threshold, and the display control unit may perform the switching between the internal measurement information output by the internal measurement unit and the information relating to the living-body information indicated by the living-body signal for display on the display unit, based on the result of the determination by the determination unit determining whether or not the information falls within the range of the predetermined threshold.

The electronic device may further include a signal acquisition control unit that performs switching between settings that activate and stop the living-body signal acquisition unit.

In the electronic device, the display control unit may cause the display unit to display whether the living-body signal acquisition unit is set to be activated or is set to be stopped.

The electronic device may further include a signal acquisition control unit that activates operation of the living-body signal acquisition unit when transition to a predetermined mode is performed.

In the electronic device, if the living-body signal acquisition unit acquires the living-body signal, the display control unit may perform the switching among multiple display patterns, in each of which the information relating to the living-body information indicated by the living-body signal is displayed, for display on the display unit, and if the living-body signal acquisition unit does not acquire a living-body signal, the display control unit may perform the switching among multiple display patterns in each of which the information relating to the internal measurement information output by the internal measurement unit is displayed, for display on the display unit.

In the electronic device, if a state where the living-body signal acquisition unit is determined as acquiring the living-body signal is changed to a state where the living-body signal acquisition unit is determined as not acquiring the living-body signal, after waiting a predetermined period of time, the display control unit may perform the switching among the multiple display patterns in each of which the internal measurement information measured by the internal measurement unit is displayed, for display on the display unit.

In the electronic device, the display control unit may cause the display unit to perform the display of the information in a display pattern that differs from one mode to another, and in a predetermined mode, performs the switching.

According to the present application, there is provided a display control method for use in an electronic device including a display unit that displays information, a living-body signal acquisition unit that acquires a living-body signal indicating a result of measuring living-body information from a measurement device that measures the living-body information, and an internal measurement unit that outputs internal measurement information that is measured within the internal measurement unit, the method including determining whether or not the living-body signal acquisition unit acquires the living-body signal and performing switching between the internal measurement information output by the internal measurement unit and information relating to the living-body information indicated by the living-body signal for display on the display unit, based on a result of the determination.

According to the present application, there is provided a program for causing a computer that controls an electronic device including a display unit that displays information, a living-body signal acquisition unit that acquires a living-body signal indicating a result of measuring living-body information from a measurement device that measures the living-body information, and an internal measurement unit that outputs internal measurement information that is measured within the internal measurement unit to execute a process, the process including determining whether or not the living-body signal acquisition unit acquires the living-body signal and performing switching between the internal measurement information output by the internal measurement unit and information relating to the living-body information indicated by the living-body signal for display on the display unit, based on a result of the determination.

According to the present application, a user's laborious job of performing a display switching operation can be reduced.

BRIEF DESCRIPTION OF THE DRAWINGS

FIG. 9 is an explanatory view illustrating a display example of the display unit in a timer mode according to the first embodiment.

FIG. 10 is an explanatory view illustrating a display example of the display unit in an alarm mode according to the first embodiment.

DETAILED DESCRIPTION OF THE INVENTION

First Embodiment

Figure 1:
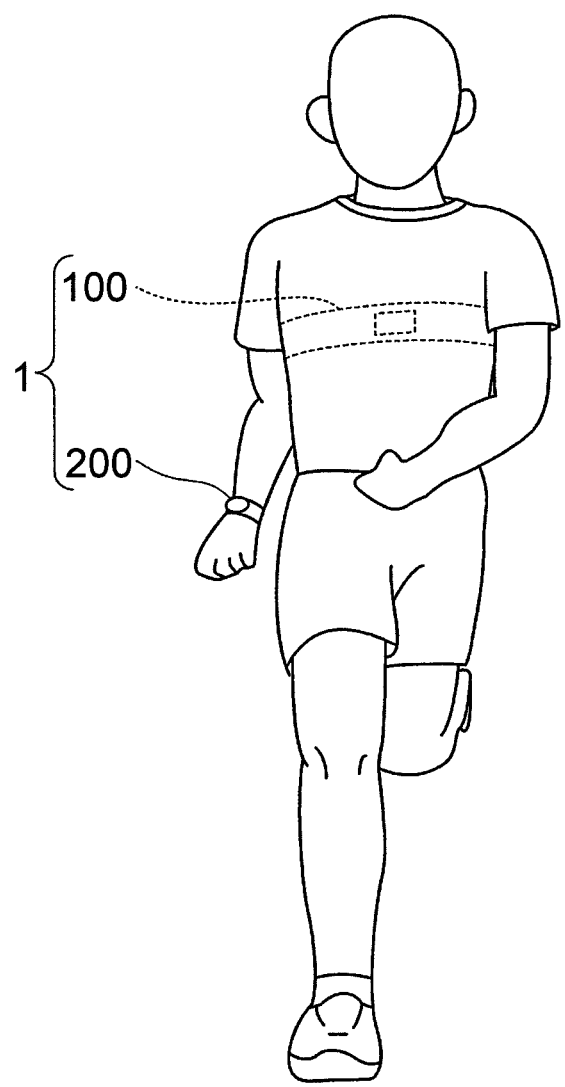
FIG. 1 is a schematic configuration diagram illustrating a system configuration of a running watch system according to a first embodiment of the present invention.

Embodiments according to the present invention are described below referring to the drawings. FIG. 1 is a schematic configuration diagram illustrating a system configuration of a running watch system according to an embodiment of the present invention. In FIG. 1, a running watch system 1 includes a chest strap 100 and a running watch 200.

The running watch system 1 provides information such as the heart rate (the number of heartbeats per minute) or a lap time to a user who participates in sports such as running.

The chest strap 100, which is attached to a user's chest, detects a user's heartbeat and transmits a heartbeat signal wirelessly to the running watch 200. The chest strap 100 corresponds to one example of a measurement device according to the present invention.

The running watch 200 displays information such as the number of heartbeats or the lap time, and thus a user is provided with the information. The running watch 200 corresponds to one example of an electronic device according to the present invention.

Specifically, the running watch 200 counts the heartbeat signal from the chest strap 100 and thus calculates the number of heartbeats and displays the calculated number of heartbeats on a display screen. The number of heartbeats corresponds to one example of living-body information according to the present invention. The living-body information is information that can be acquired by measuring the living body. The heartbeat detected by the chest strap 100 also corresponds to one example of the living-body information according to the present invention. Furthermore, the heartbeat signal transmitted by the chest strap 100 corresponds to one example of a living-body signal according to the present invention.

Furthermore, the running watch 200 displays a point in time, a lap time, or a split time on a display screen. The point in time, the lap time, or the split time corresponds to one example of time-related information according to the present invention. The time-related information here is information that can be acquired by measuring the time. For example, a current point in time can be acquired by adding time that elapses from a point in time as a reference, to the point in time as the reference. The point in time, the lap time, and the split time are collectively hereinafter referred to as time information.

At this point, the running watch 200 switches between the number of heartbeats and the time information in order to display either of the number of heartbeats and the time information. Accordingly, the running watch 200 effectively uses a display region that is limited in an amount of display-enabled information and thus can display the information that the user desires.

However, a scope of application of the present invention is not limited to the running watch system. The present invention can be applied to various electronic devices that display the living-body information and the time-related information on the limited display region. For example, the present invention may be applied to a treadmill in which the number of heartbeats and the point in time is switched to be displayed on the region that is limited in display screen.

Furthermore, the living-body information according to the present invention is not limited to the number of heartbeats, and various types of living-body information can be set such as respiration rate or energy consumption.

Furthermore, a way by which the measurement device according to the present invention transmits the living-body signal to an electronic device is not limited to wireless communication, and cable communication may be possible. Furthermore, the measurement device may be incorporated into the electronic device.

Figure 2:
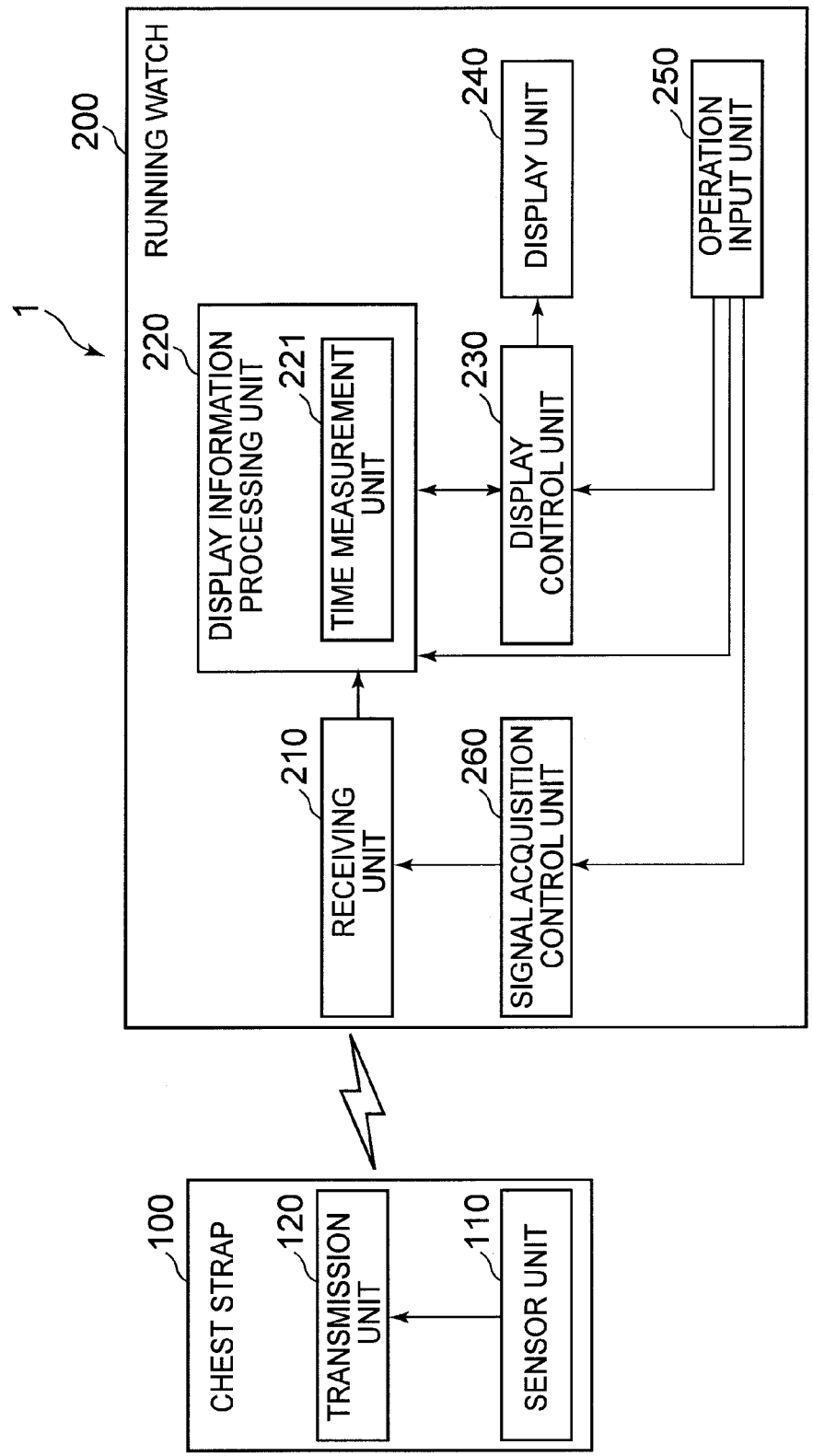
FIG. 2 is a schematic block diagram illustrating a functional configuration of the running watch system according to the first embodiment.

FIG. 2 is a schematic block diagram illustrating a functional configuration of the running watch system 1. In FIG. 2, a running watch system 1 includes a chest strap 100 and a running watch 200. The chest strap 100 includes a sensor unit 110 and a transmission unit 120. The running watch 200 includes a receiving unit 210, a display information processing unit 220, a display control unit 230, a display unit 240, an operation input unit 250, and a signal acquisition control unit 260. The display information processing unit 220 includes a time measurement unit 221.

The sensor unit 110 has a heartbeat sensor and outputs the heartbeat signal to the transmission unit 120 each time a user's heartbeat is detected.

The transmission unit 120 wirelessly transmits the heartbeat signal that is output by the sensor unit 110.

The receiving unit 210 corresponds to one example of a living-body signal acquisition unit according to the present invention and acquires the living-body signal indicating a result of measuring the living-body information from the measurement device that measures the living-body information. Specifically, the receiving unit 210 receives the heartbeat signal from the chest strap 100 (the transmission unit 120) and thus outputs the received heartbeat signal to the display information processing unit 220.

The display information processing unit 220 calculates the number of heartbeats, based on the heartbeat signal received by the receiving unit 210. Furthermore, the display information processing unit 220 measures the time information in the time measurement unit 221. Furthermore, the display information processing unit 220 stores the calculated number of heartbeats and the measured time information, depending on a user operation. Then, the display information processing unit 220 outputs the information to be displayed on the display unit 240 to the display control unit 230, depending on the user operation detected by the operation input unit 250.

The time measurement unit 221 has an oscillator that generates a clock signal and performs the time measurement using the clock signal and thus measures the time information.

The operation input unit 250 has a push button and detects the user operation of pushing down the push button.

The signal acquisition control unit 260 performs switching between settings that activate and stop the receiving unit 210, based on the user operation detected by the operation input unit 250. Because the signal acquisition control unit 260 performs the switching, power consumption can be reduced when the measurement of the number of heartbeats is not performed.

For example, when the user participates in a race, it is considered that for example, a split-time display function of the running watch 200 is used without wearing the chest strap 100. In such a case, the operation input unit 250 is responsive to the user operation for the setting that stops the receiving unit 210 and the signal acquisition control unit 260 can suppress power consumption by the receiving unit 210 by stopping the receiving unit 210, depending on the user operation.

The display unit 240 has the display screen and displays the information that is output by the display information processing unit 220, such as the number of heartbeats or the time information, depending on the control by the display control unit 230.

The display control unit 230 controls the display unit 240 and thus displays various types of information. Particularly, the display control unit 230 performs switching between the time information and the number of heartbeats for display on the display unit 240, based on whether or not the receiving unit 210 receives the heartbeat signal. Moreover, the display control unit 230 causes the display unit 240 to perform information display in different patterns for every mode and performs the switching between the time information and the number of heartbeats for display on the display unit 240, in a predetermined mode. Moreover, if the receiving unit 210 acquires the heartbeat signal, the display control unit 230 performs switching among the multiple display patterns in each of which the number of heartbeats is displayed, for display on the display unit 240. On the other hand, if the receiving unit 210 does not acquire the heartbeat signal, the display control unit 230 performs switching among the multiple display patterns in each of which the time information is displayed, for display on the display unit 240. A specific example of the display switching performed by the display control unit 230 is described below.

Furthermore, the display control unit 230 causes the display unit 240 to perform the display of whether the setting by the signal acquisition control unit 260 is the setting that activates the receiving unit 210 or the setting that stops the receiving unit 210. A specific example of the display is described below.

Figure 3:
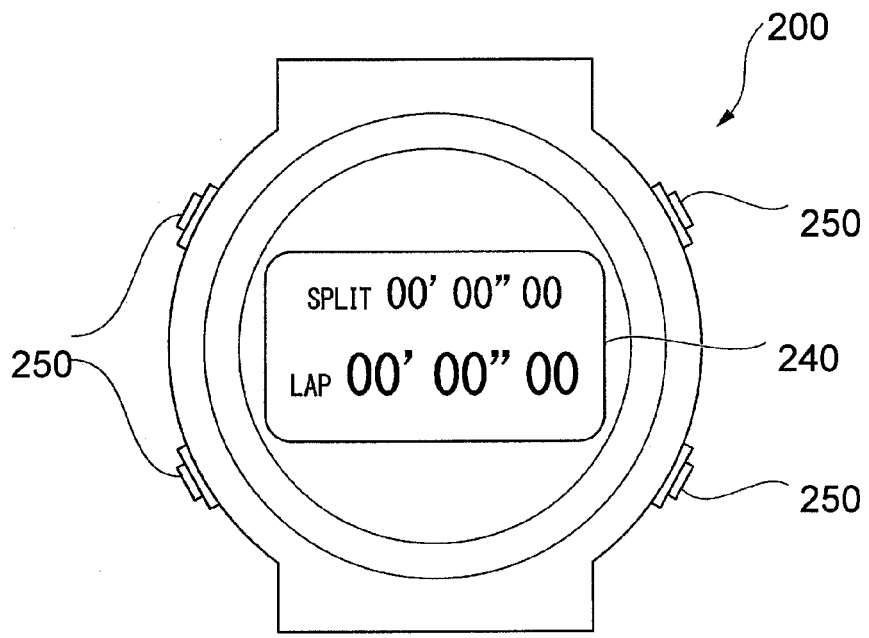
FIG. 3 is an external-form diagram illustrating an outlined external form of a main body of a running watch according to the first embodiment.

FIG. 3 is an external-form diagram illustrating an outlined external form of a main body of the running watch 200. FIG. 3 illustrates the display screen of the display unit 240 and the push button of the operation input unit 250.

The display screen of the display unit 240 is limited in the amount of display-enabled information. Specifically, the display unit 240 displays two items of information, one on the upper portion and the other on the lower portion as illustrated in FIG. 3. Then, the display unit 240 switches among display items, depending on the control by the display control unit 230, and performs the information display.

Furthermore, with the pushing-down of the push button illustrated in FIG. 3, the operation input unit 250 is responsive to the user operation, such as switching among the modes, switching among the display patterns in the mode, switching between the settings that activate and stop the receiving unit 210, recording of the lap time or the split time, or time adjustment.

Next, the modes of the running watch 200 and the display in each mode are described referring to FIGS. 4 to 10.

Figure 4:
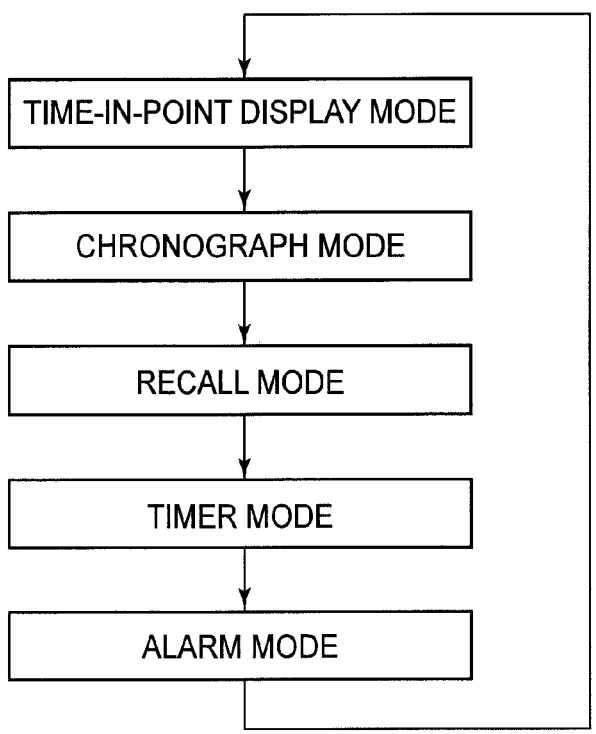
FIG. 4 is an explanatory view illustrating a mode transition in the running watch according to the first embodiment.

FIG. 4 is an explanatory view illustrating a mode transition in the running watch 200. As illustrated in FIG. 4, each time the operation input unit 250 detects the user operation for the switching among the modes, the running watch 200 (the display information processing unit 220) provides a transition in this sequence: a point-in-time display mode, a chronograph mode, a recall mode, a timer mode, an alarm mode. Then, in the alarm mode, when the operation input unit 250 detects the user operation for the switching among the modes, the running watch 200 (the display information processing unit 220) returns to the point-in-time display mode.

Figure 5:
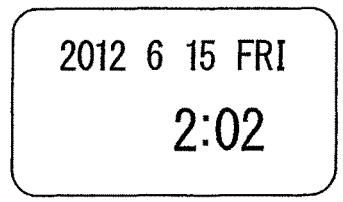
FIG. 5 is an explanatory view illustrating a display example of a display unit in a point-in-time display mode according to the first embodiment.

FIG. 5 is an explanatory view illustrating a display example of the display unit 240 in the point-in-time display mode. As illustrated in FIG. 5, in the point-in-time display mode, the display unit 240 displays the current date in the year-month-day format and in the day-of-the-week format on the upper portion and the current point in time on the lower portion.

Figure 6:
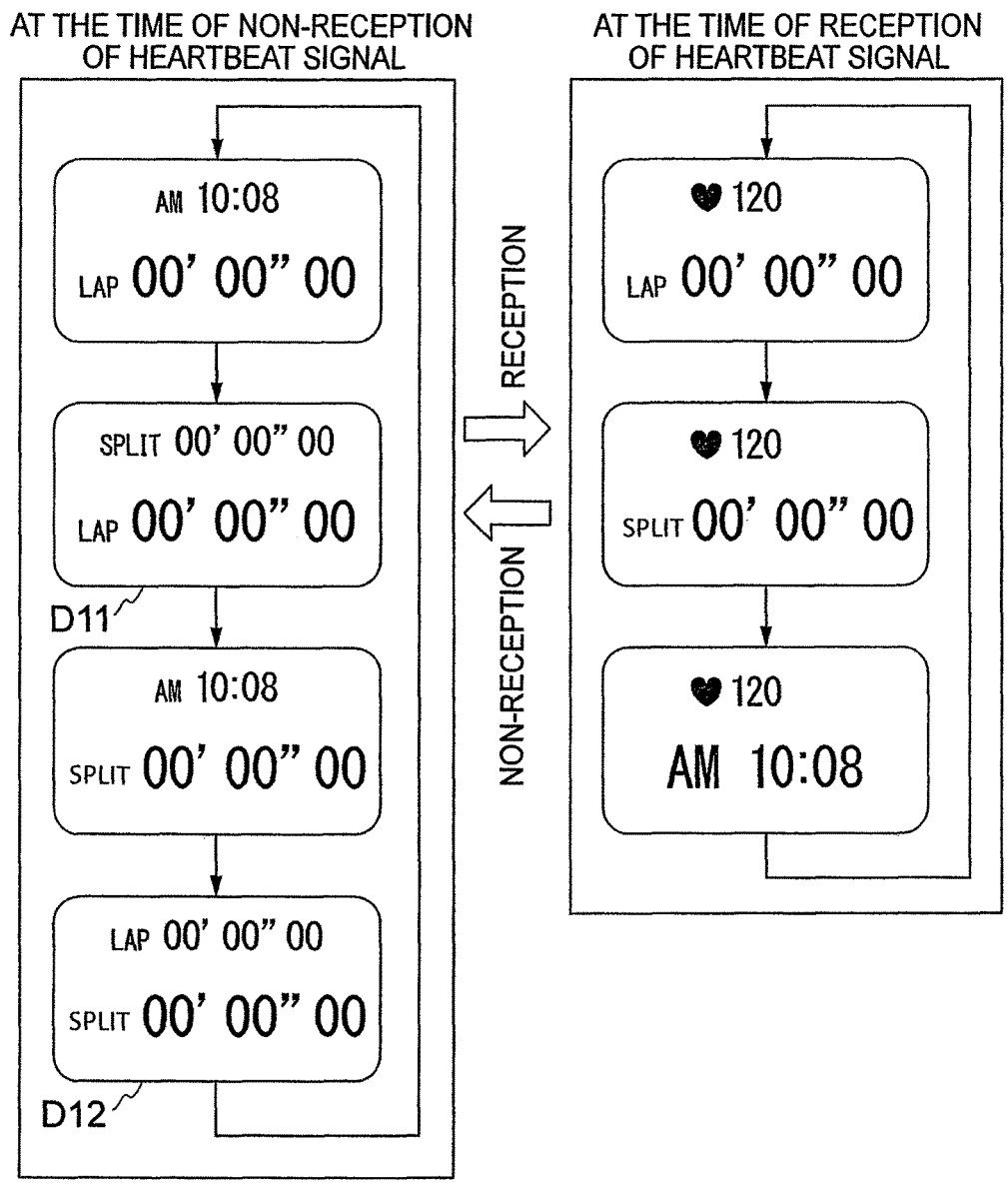
FIG. 6 is an explanatory view illustrating a display example of the display unit in a chronograph mode according to the first embodiment.

FIG. 6 is an explanatory view illustrating the display example of the display unit 240 in the chronograph mode. The running watch 200 (the display unit 240) performs the lap-time or split-time display in the chronograph mode.

As illustrated in FIG. 6, in the chronograph mode, the display unit 240 switches among the display patterns, depending on whether the receiving unit 210 receives the heartbeat signal. Furthermore, each time the operation input unit 250 detects the user operation for the switching among the display patterns, the display unit 240 switches among the display patterns.

Moreover, timing when the display unit 240 switches among the display patterns is not limited to timing when the operation input unit 250 detects the user operation for the switching among the display patterns. For example, the display unit 240 may perform the switching among the display patterns for every predetermined period of time for the display, depending on the control by the display control unit 230.

When the heartbeat signal is not received, the display unit 240 switches among the current point in time, the lap time, and the split time for the display. In this manner, the display unit 240 displays the time information both on the upper portion and on the lower portion. At this point, characters on the lower portion are larger in size than those on the upper portion and thus are easy for the user to view. Then, the display unit 240 displays the split time and the lap time on the upper and lower portions or on the lower and upper portions, respectively. For example, in a display example D11, the display unit 240 displays the split time on the upper portion and the lap time on the lower portion, and in contrast, in a display example D12, the display unit 240 displays the lap time on the upper portion and displays the split time on the lower portion.

On the other hand, when receiving the heartbeat signal, the display unit 240 displays the number of heartbeats on the upper portion and switches between the lap time, the split time, and the current point in time for the display on the lower portion.

In this manner, when receiving or not receiving the heartbeat signal, the display unit 240 switches between the number of heartbeats and the time information for display on the upper portion.

The determination of whether the heartbeat signal is received or not received is performed, for example, by the display information processing unit 220. Depending on the presence or absence of an output of the heartbeat signal from the receiving unit 210, when the output of the heartbeat signal is absent for a predetermined period of time (for example, one minute) or more, the display information processing unit 220 determines the absence of the output of the heartbeat signal as the non-reception of the heartbeat signal and determines the other cases (that is, when the output of the heartbeat signal is present within the predetermined period of time) as the reception of the heartbeat signal. Then, the display information processing unit 220 performs the display switching on the display unit 240, depending on the result of the determination.

When switching between the number of heartbeats and the time information, the display control unit 230 selects, for example, the display pattern in which a change is not present on the lower-portion display. For example, the display control unit 230 controls the display unit 240 in such a manner that the number of heartbeats is displayed on the upper portion and the lap time is continuously displayed on the lower portion in performing the switching from the display (a display example D11) at the time of the non-reception of the heartbeat signal, in which the split time is displayed on the upper portion and the lap time is displayed on the lower portion to display at the time of the reception of the heartbeat signal.

Even though the switching is performed from the display at the time of the reception of the number of heartbeats to display at the time of the non-reception of the number of heartbeats, the display control unit 230 selects the display pattern in which the change is not present on the lower-portion display and performs the display on the display unit 240.

Moreover, a display position of the number of heartbeats at the time of the reception of the heartbeat signal is not limited to an upper-position fixation illustrated in an example in FIG. 6. The display unit 240 may display the number of heartbeats on the lower portion or may switch between the upper portion and the lower portion to display the number of heartbeats on either of the upper portion and the lower portion (that is, the display pattern in which the number of heartbeats is displayed on the upper portion and the display pattern in which the number of heartbeats is displayed on the lower portion are both available). Alternatively, the user may choose between the upper-portion fixation, a lower-portion fixation, and a switch between the upper-portion and the lower-portion.

The display unit 240 fixes the display of the number of heartbeats to either the upper portion or the lower portion. That is, the display unit 240 displays the number of heartbeats on the fixed position. Thus, the user can grasp the display of the number of heartbeats more easily.

On the other hand, the display unit 240 switches between the upper portion and the lower portions for the display position of the number of heartbeats, and thus the user can set the display position, depending on the information that he or she preferentially desires to view. Specifically, when the user preferentially desires to view the number of heartbeats, he or she can easily view the number of heartbeats by causing the number of heartbeats to be displayed on the lower portion. On the other hand, when the user desires to view the time information preferentially, he or she can easily view the time information that is displayed on the lower portion by causing the number of heartbeats to be displayed on the upper portion.

At this point, a case where the receiving unit 210 is set to be stopped and a case where the receiving unit 210 is set to be activated, but the chest strap 100 (the transmission unit 120) does not transmit the heartbeat signal or although the chest strap 100 transmits the heart signal, the receiving unit 210 cannot detect the heartbeat signal are considered as a case where the receiving unit 210 is in a state of the non-reception of the heartbeat signal. Then, in a case where the receiving unit 210 is in the state of the non-reception of the heartbeat signal, the display unit 240 performs the display of whether the receiving unit 210 is set to be activated or is set to be stopped, depending on the control by the display control unit 230.

Figure 7:
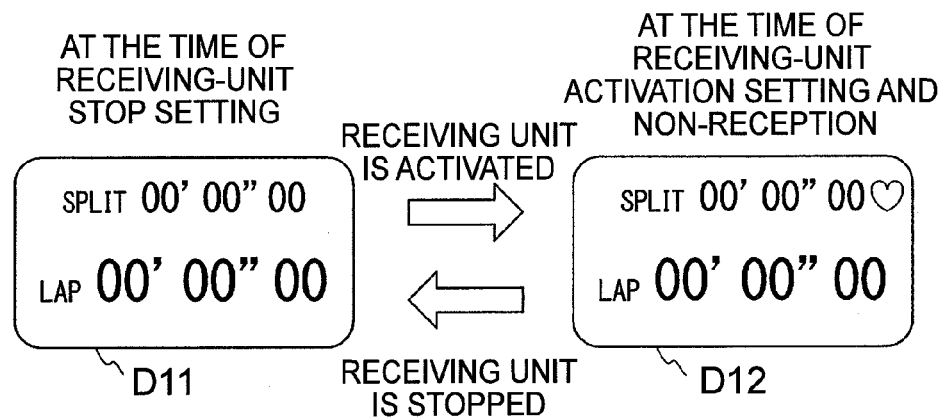
FIG. 7 is an explanatory view illustrating an example that displays whether a receiving unit is set to be activated or is set to be stopped according to the first embodiment.

FIG. 7 is an explanatory view illustrating an example that displays whether the receiving unit 210 is set to be activated or is set to be stopped. A display example D11 in FIG. 7 is a display example in which in the same manner as in FIG. 6, the split time is displayed on the upper portion and the lap time is displayed on the lower portion. The display example D11 is a display example in which the receiving unit 210 is set to be stopped. On the other hand, a display example D21 is a display example in which the receiving unit 210 is set to be activated.

In the display example D21, the display unit 240 indicates that the receiving unit 210 is set to be activated by displaying a solid-white heart mark. On the other hand, in the display example D11, the display unit 240 does not display the heart mark and with this non-display of the heart mark, indicates that the receiving unit 210 is set to be stopped.

In this manner, the display unit 240 displays whether the receiving unit 210 is set to be activated or is set to be stopped, and thus the user can perform a proper response if he or she desires to cause the number of heartbeats to be displayed. Specifically, if the receiving unit 210 is set to be stopped, the user performs the operation in which the receiving unit 210 is set to be activated. On the other hand, despite the fact that the receiving unit 210 is set to be activated, if the number of heartbeats is not displayed, for example, a cause, such as the chest strap not being correctly worn, is considered. Then, the user takes action to wear the chest strap correctly.

Moreover, FIG. 7 illustrates a display example only of the display pattern (the display example D11) in which the split time is displayed on the upper portion and the lap time is displayed on the lower portion, from among the display patterns at the time of the non-reception of the heartbeat signal illustrated in FIG. 6, but the same is true for the other display patterns as well. That is, for any of the display patterns at the time of the non-reception of the heartbeat signal which are illustrated in FIG. 6, the display unit 240 displays whether the receiving unit 210 is set to be activated or is set to be stopped, depending on whether or not the solid-white heart mark is displayed.

Figure 8:
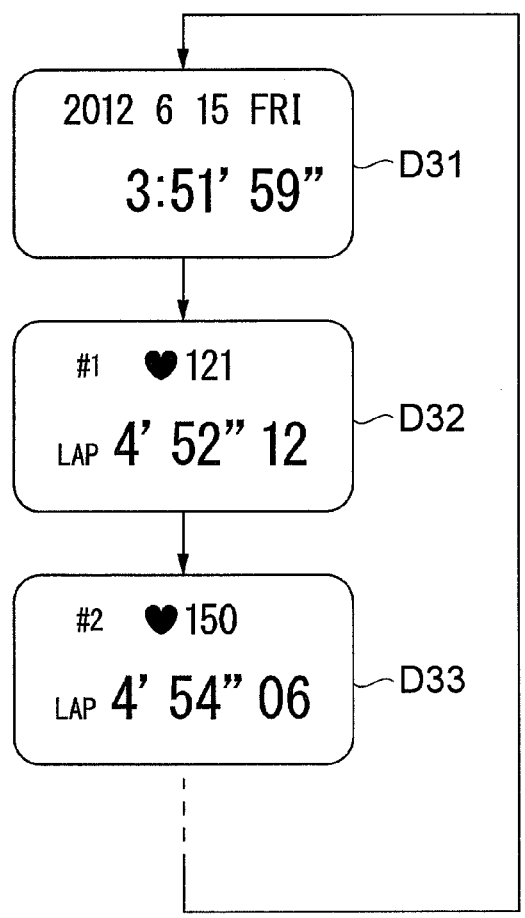
FIG. 8 is an explanatory view illustrating a display example of the display unit in a recall mode according to the first embodiment.

FIG. 8 is an explanatory view illustrating a display example of the display unit 240 in the recall mode. In the recall mode, the running watch 200 (the display unit 240) performs the display of the information that is stored by the display information processing unit 220.

A display example D31 in FIG. 8 is a display example of an initial screen in the recall mode. On the initial screen, the display unit 240 displays a date at which the measurement is performed, in the year-month-day format and in the day-of-the-week format on the upper portion and displays a total measurement time on the lower portion.

In a state where the display unit 240 displays the initial screen, when the operation input unit 250 detects the user operation for the display switching, the display unit 240 displays the information that is first stored by the display information processing unit 220.

A display example D32 is a display example of the information that is first stored by the display information processing unit 220. In the display example D32, the display unit 240 displays the number of heartbeats on the upper portion and the lap time on the lower portion, as the information that is first stored by the display information processing unit 220 depending on the user operation for the information retention.

In a state where the display unit 240 displays the information first stored by the display information processing unit 220, when the operation input unit 250 detects the user operation for the display switching, the display unit 240 displays the information that is second stored by the display information processing unit 220.

A display example D33 is a display example of the information that is second stored by the display information processing unit 220. In the display example D33, the display unit 240 displays the number of heartbeats on the upper portion and displays the lap time on the lower portion as the information that is second stored by the display information processing unit 220 depending on the user operation for the information retention.

In this manner, each time the operation input unit 250 detects the user operation for the display switching, the display unit 240 displays the information in order that the display information processing unit 220 stores the information. In a state where the information last stored by the display information processing unit 220 is displayed, when the operation input unit 250 detects the user operation for the display switching, the display returns to the initial screen illustrated in the display example D31.

Figures 9, 10:
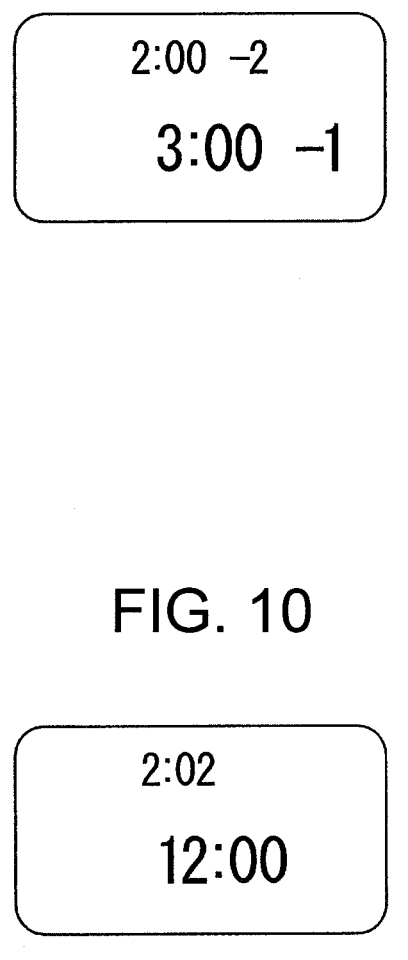

FIG. 9 is an explanatory view illustrating a display example of the display unit 240 in the timer mode. The time measurement unit 221 has a timer function for two timers (a first timer and a second timer), and the display unit 240 displays the remaining time on the second timer on the upper portion and the remaining time on the first timer on the lower portion.

Moreover, in addition to the chronograph mode, or instead of the chronograph mode, the display unit 240 may display the number of heartbeats in the timer mode. For example, when the user has training with the training time being fixed, such as an interval training, the display unit 240 displays the timer and the number of heartbeats, and thus the user can have the training while checking the number of heartbeats, without performing the operation for the display switching.

Also in the display of the number of heartbeats in the timer mode, the display control unit 230 switches between the presence and the absence of the display of the number of heartbeats, depending on the presence and the absence of the reception of the heartbeat signal, in the same manner as in the chronograph mode as described referring to FIG. 6. Furthermore, in the same manner as described referring to FIG. 7, the display unit 240 may display whether the receiving unit 210 is set to be activated or is set to be stopped, depending on the control by the display control unit 230.

Furthermore, in the same manner as in the chronograph mode, also in the timer mode, the display unit 240 may display the number of heartbeats on the upper portion, display the number of heartbeats on the lower portion, or switch between the upper portion and the lower portion for the display on either of the upper portion and the lower portion. For example, the display unit 240 may switch from the display of the timer on the upper portion or the lower portion on which the timer does not operate to the display of the number of heartbeats.

Alternatively, the user may choose between the upper-portion fixation, the lower-portion fixation, and the switch between the upper-portion and the lower-portion, with respect to the display position of the number of heartbeats.

FIG. 10 is an explanatory view illustrating a display example of the display unit 240 in the alarm mode. The running watch 200 (the display information processing unit 220) performs the setting of the point in time for alarm in the alarm mode.

As illustrated in FIG. 10, in the alarm mode, the display unit 240 displays the current point in time on the upper portion and displays the point in time for alarm on the lower portion. Then, the point in time for alarm is set based on the user operation for the setting of the point in time for alarm, which is detected by the operation input unit 250.

Figure 11:
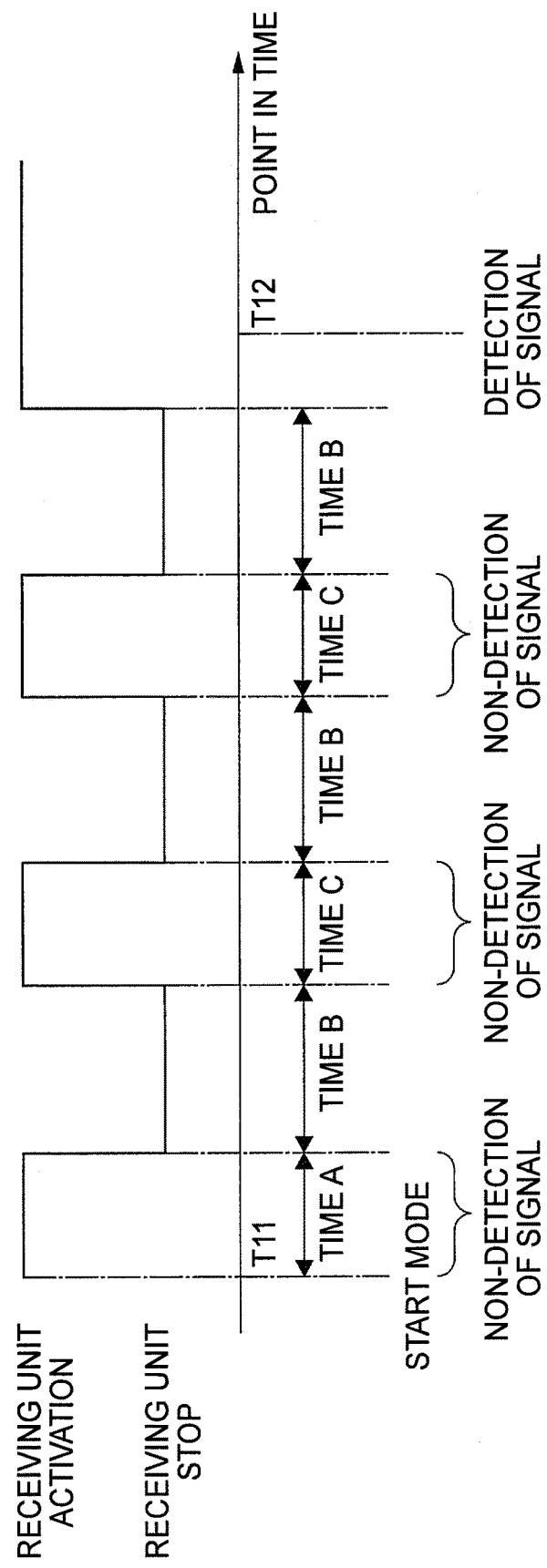
FIG. 11 is an explanatory view illustrating an example in which power supply to the receiving unit is stopped in a case where the receiving unit is set to be activated according to the first embodiment.

Next, suppression of power consumption by the receiving unit 210 is described referring to FIG. 11.

FIG. 11 is an explanatory view illustrating an example in which power supply to the receiving unit 210 is stopped in a case where the receiving unit 210 is set to be activated. In a case where the heartbeat signal is not received although the receiving unit 210 is set to be activated, the signal acquisition control unit 260 suppresses the power consumption by the receiving unit 210 by temporarily stopping the receiving unit 210.

In an example in FIG. 11, at the point in time T11, the mode of the running watch 200 performs a transition from the point-in-time display mode to the chronograph mode. In this manner, when the transition to the chronograph mode is performed, the signal acquisition control unit 260 starts the operation of the receiving unit 210 and awaits the heartbeat signal for a predetermined period of time A (for example, one minute). The same is true for the switching from the setting that stops the receiving unit 210 to the setting that activates the receiving unit 210.

At this point, if the receiving unit 210 detects the heartbeat signal for the period of time A, the signal acquisition control unit 260 maintains a state where the receiving unit 210 is activated. On the other hand, if the receiving unit 210 does not detect the heartbeat signal, the signal acquisition control unit 260 reduces the power consumption by temporarily stopping the receiving unit 210 for a predetermined period of time B (for example, two minutes).

In an example in FIG. 11, the receiving unit 210 does not detect the heartbeat signal for the period of time A and stops the receiving unit 210 for the period of time B.

When the period of time B elapses, the signal acquisition control unit 260 again activates the receiving unit 210 and awaits the heartbeat signal for a period of time C (for example, one minute). If the receiving unit 210 detects the heartbeat signal for the period of time C, the signal acquisition control unit 260 maintains a state where the receiving unit 210 is activated. On the other hand, if the receiving unit 210 does not detect the heartbeat signal, the signal acquisition control unit 260 temporarily stops the receiving unit 210, activates the receiving unit 210 each time the period of time B elapses, and repeats the processing in which the heartbeat signal is awaited, for the period of time C.

In an example in FIG. 11, the receiving unit 210 detects the heartbeat signal at the point in time T12, and thereafter the signal acquisition control unit 260 maintains a state where the receiving unit 210 is activated.

In a state where the receiving unit 210 is activated, even though the receiving unit 210 does not detect the heartbeat signal for a period of time D (for example, two minutes), the signal acquisition control unit 260 reduces the power consumption by temporarily stopping the receiving unit 210. Then, the signal acquisition control unit 260 repeats the processing in which the heartbeat signal is awaited, for the period of time C, by activating the receiving unit 210 each time the period of time B elapses.

As described above, the display control unit 230 performs the switching between the time information and the number of heartbeats for display on the display unit 240, based on whether or not the receiving unit 210 receives the heartbeat signal.

Accordingly, if the user desires to view the number of heartbeats, he or she can display the number of heartbeats on the running watch 200 (the display unit 240) by wearing the chest strap and causing the heartbeat signal to be transmitted. On the other hand, if there is no need to view the number of heartbeats, the user can cause the time information to be displayed on the running watch 200 (the display unit 240) instead of the number of heartbeats by not wearing the chest strap. Therefore, the user does not need to perform the user operation for switching between the display of the time information and the display of the number of heartbeats. In this respect, with the running watch system 1 (the running watch 200), a user's laborious job of performing a display switching operation can be reduced.

Furthermore, the signal acquisition control unit 260 performs the switching between the setting that activates the receiving unit 210 and the setting that stops the receiving unit 210.

Accordingly, if the number of heartbeats does not need to be displayed, the signal acquisition control unit 260 can reduce the power consumption by stopping the receiving unit 210. Furthermore, the stopping of the receiving unit 210 prevents the number of heartbeats from being acquired, and the display control unit 230 causes the display unit 240 to display the time information instead of the number of heartbeats. Therefore, the user does not need to perform the user operation for switching between the display of the time information and the display of the number of heartbeats and can cause the display unit 240 to display the time information.

Furthermore, when the transition to a predetermined mode (the chronograph mode) is performed, the signal acquisition control unit 260 causes the receiving unit 210 to start a living-body signal acquisition operation.

Accordingly, the signal acquisition control unit 260 can cause the receiving unit 210 to acquire the living-body signal at the timing when the acquisition of the living-body signal is necessary depending on the user operation for mode switching, and furthermore, when the acquisition of the living-body signal is unnecessary, can reduce the power consumption by stopping the receiving unit 210.

Furthermore, the display control unit 230 causes the display unit 240 to display whether the receiving unit 210 is set to be activated or is set to be stopped.

Accordingly, if the user desires to cause the running watch 200 (the display unit 240) to display the number of heartbeats, he or she can perform a proper response.

Furthermore, if the receiving unit 210 receives the heartbeat signal, the display control unit 230 performs the switching among the multiple display patterns in each of which the number of heartbeats is displayed, for display on the display unit 240. On the other hand, if the receiving unit 210 does not acquire the heartbeat signal, the display control unit 230 performs the switching among the multiple display patterns in each of which the time information is displayed, for display on the display unit 240.

Accordingly, in a state where depending on whether or not the user desires the display of the number of heartbeats, the switching is made between the display of the number of heartbeats and the display of the time information, the display control unit 230 switches to the time information for the display. In this respect, the display control unit 230 can cause the information desired by the user to be displayed on the display unit 240 more properly.

Furthermore, the display control unit 230 causes the display unit 240 to perform the display of the information in the display pattern that differs from one mode to another, and in the predetermined mode (the chronograph mode), performs the switching between the time information and the number of heartbeats for display on the display unit 240.

Accordingly, the display control unit 230 can distinguish between the mode (the function) in which the number of heartbeats needs to be displayed and the mode in which the number of heartbeats does not need to be displayed. In this respect, the display control unit 230 can cause the display unit 240 to perform the appropriate display, depending on whether or not the user desires to display the number of heartbeats.

Second Embodiment

Figure 12:
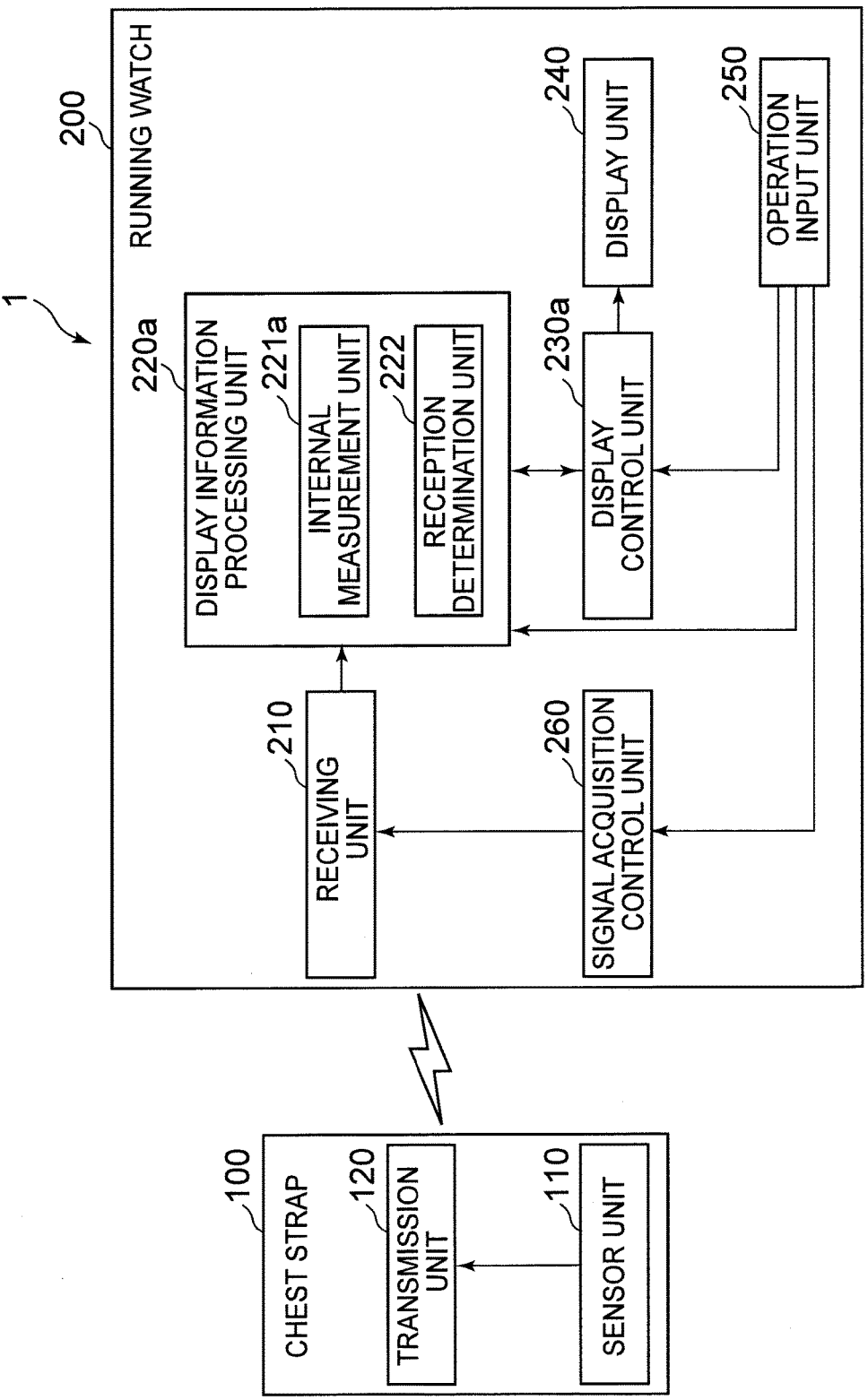
FIG. 12 is a schematic block diagram illustrating a functional configuration of a running watch system according to a second embodiment of the present invention.

A second embodiment is described in detail below. FIG. 12 is a schematic block diagram illustrating a functional configuration of a running watch system 1 according to the second embodiment. In FIG. 12, the same reference numerals as those in FIG. 2 are used in a configuration that is in common with the first embodiment, and a description of the configuration is omitted. The running watch system 1 includes a chest strap 100 and a running watch 200. The chest strap 100 includes a sensor unit 110 and a transmission unit 120. The running watch 200 includes a receiving unit 210, a display information processing unit 220a, a display control unit 230a, a display unit 240, an operation input unit 250, and a signal acquisition control unit 260. The display information processing unit 220a includes an internal measurement unit 221a and a reception determination unit 222.

In the running watch 200 according to the second embodiment, the reception determination unit 222 to be described below performs a determination of whether or not the receiving unit 210 receives a living-body signal, instead of the display information processing unit 220. Moreover, the living-body signal, for example, is a heartbeat signal, but is not limited to the heartbeat signal. The living-body signal may be any information that can be obtained by measuring a living body, such as a pulse signal or a signal indicating blood pressure, or a combination of these. Furthermore, in the running watch 200 according to the second embodiment, the internal measurement unit 221a to be described below measures internal measurement information, instead of the time measurement unit 221 that measures the time information. The internal measurement information includes information that is measured within the running watch 200 and information that is calculated based on the measured information. Specifically, the internal measurement information is information including at least one of a point in time, a time, the number of steps, steps per minute (SPM), walking or running acceleration, a walking or running distance, energy consumed during walking or running, and so on.

The display information processing unit 220a includes the internal measurement unit 221a and the reception determination unit 222. The display information processing unit 220a calculates living-body information, based on the living-body signal received by the receiving unit 210. The living-body information, for example, is information calculated from the living-body signal, such as the number of heartbeats, a pulse rate, a change in blood pressure, and so on and is any one of the items of information or a combination of two or more of the items of information. For example, if the living-body signal is the heartbeat signal, the display information processing unit 220a calculates the number of heartbeats, that is, the living-body information, using Expression (1) that follows, based on time interval $\Delta T[s]$ of the living-body signal.

$$\text{(the number of heartbeats)} = 60/\Delta T \text{ [bpm]} \qquad (1)$$

Furthermore, the display information processing unit 220a measures the internal measurement information with the internal measurement unit 221a. Furthermore, the display information processing unit 220a determines whether or not the receiving unit 210 receives the living-body signal, with the reception determination unit 222 to be described below. Moreover, if the reception determination unit 222 determines that the living-body signal is received, the display information processing unit 220a determines whether or not the living-body information calculated based on the received living-body signal falls within a range of a predetermined threshold. Specifically, if the living-body signal is the heartbeat signal, the display information processing unit 220a, for example, determines whether or not the number of heartbeats calculated from Expression (1) falls within a range of 20 to 250 [bpm]. With this determination, the display information processing unit 220a can prevent the living-body signal from being continuously measured in an abnormal reception state such as when noise gets mixed in with the living-body signal received by the receiving unit 210. Then, the display information processing unit 220a outputs the information to be displayed on the display unit 240 to the display control unit 230a, depending on the result of the determination. Furthermore, the display information processing unit 220a includes a storage unit that stores the calculated number of heartbeats or the internal measurement information measured by the internal measurement unit 221a, depending on the user operation. Then, the display information processing unit 220a outputs the information to be displayed on the display unit 240 to the display control unit 230a, depending on the user operation that is detected by the operation input unit 250.

At this point, the switching by the display control unit 230a for display on the display unit 240 is described in more detail. The display control unit 230a performs the following switching operation for the display in addition to the switching operation for display on the display unit 240 by the display control unit 230 according to the first embodiment. If the reception determination unit 222 included in the display information processing unit 220a determines that a state where the living-body signal is not received is changed to a state where the living-body signal is received, the display control unit 230a immediately performs the switching from the display of the internal measurement information that is displayed until just before the switching to the display of the living-body information. Immediately performing the switching means that the switching is performed without the timer determining whether the time has elapsed, or that the switching is performed in an extremely short amount of time. Accordingly, the running watch 200 can immediately notify the user that the living-body signal is received. Furthermore, if the reception determination unit 222 determines that the living-body signal is received, and additionally if the display information processing unit 220a determines that the living-body information calculated from the living-body signal falls within a range of a predetermined threshold, the display control unit 230a immediately performs the switching from the display of various types of information that are displayed until just before the switching to the display of the living-body information.

Furthermore, if the reception determination unit 222 determines that the state where the living-body signal is received is changed to the state where the living-body signal is not received, when a predetermined period of time T1 elapses from the time when the determination is made, the display control unit 230a performs the switching from the display of the living-body information that is displayed until just before the switching to the display of the internal measurement information. The predetermined period of time T1, for example, is a time of approximately one minute. Moreover, if the reception determination unit 222 determines that the information relating to the living-body signal does not fall within the range of the predetermined threshold, when the predetermined period of time T1 elapses from the time when the determination is made, the display control unit 230a performs the switching from the display of the living-body information that is displayed until just before the switching to the display of the internal measurement information. Accordingly, because the display of the living-body information is maintained for the predetermined period of time T1, even though the signal received from the chest strap 100 is not stable, the running watch 200 can prevent the display from being frequently switched. Moreover, if the number of the living-body information that is displayed on the display unit 240 is two or more, the display control unit 230a may cause the multiple items of living-body information to be displayed on the display region of the display unit 240 at the same time, may switch the living-body information that is periodically displayed depending on the user operation from the operation input unit 250, and may switch the living-body information that is periodically displayed each time a predetermined period of time T2 elapses. The predetermined period of time T2, for example, is a time of approximately five seconds.

The internal measurement unit 221a corresponds to one example of the internal measurement unit according to the present invention and measures the internal measurement information. Specifically, the internal measurement unit 221a has an oscillator that generates a clock signal, and by performing the measurement of the time using the clock signal, measures the point-in-time information or the time information and outputs the result of the measurement as the internal measurement information. Furthermore, the internal measurement unit 221a has an acceleration sensor and may measure the acceleration of the running watch 200, and based on the measured acceleration, may measure the number of steps and output the result of the measurement as the internal measurement information. Furthermore, the internal measurement unit 221a may measure, for example, a distance that the user walks, a distance that the user runs, calories that the user consumes, and so on, based on the calculated number of steps, and may output the result of the measurement as the internal measurement information.

Depending on the presence or absence of an output of the living-body signal from the receiving unit 210, when the output of the living-body signal is absent for a predetermined period of time (for example, one minute) or more, the reception determination unit 222 determines the absence of the output of the living-body signal as the non-reception of the living-body signal and determines the other cases (that is, when the output of the living-body signal, although present one time, is present within the predetermined period of time) as the reception of the living-body signal. Moreover, the reception determination unit 222 may perform the determination described above, depending on whether or not the living-body signal is continuously received with a predetermined period within a predetermined period of time. At this point, the display information processing unit 220a described above and the reception determination unit 222 included in the display information processing unit 220a are one example of a determination unit according to the present invention.

Figure 13:
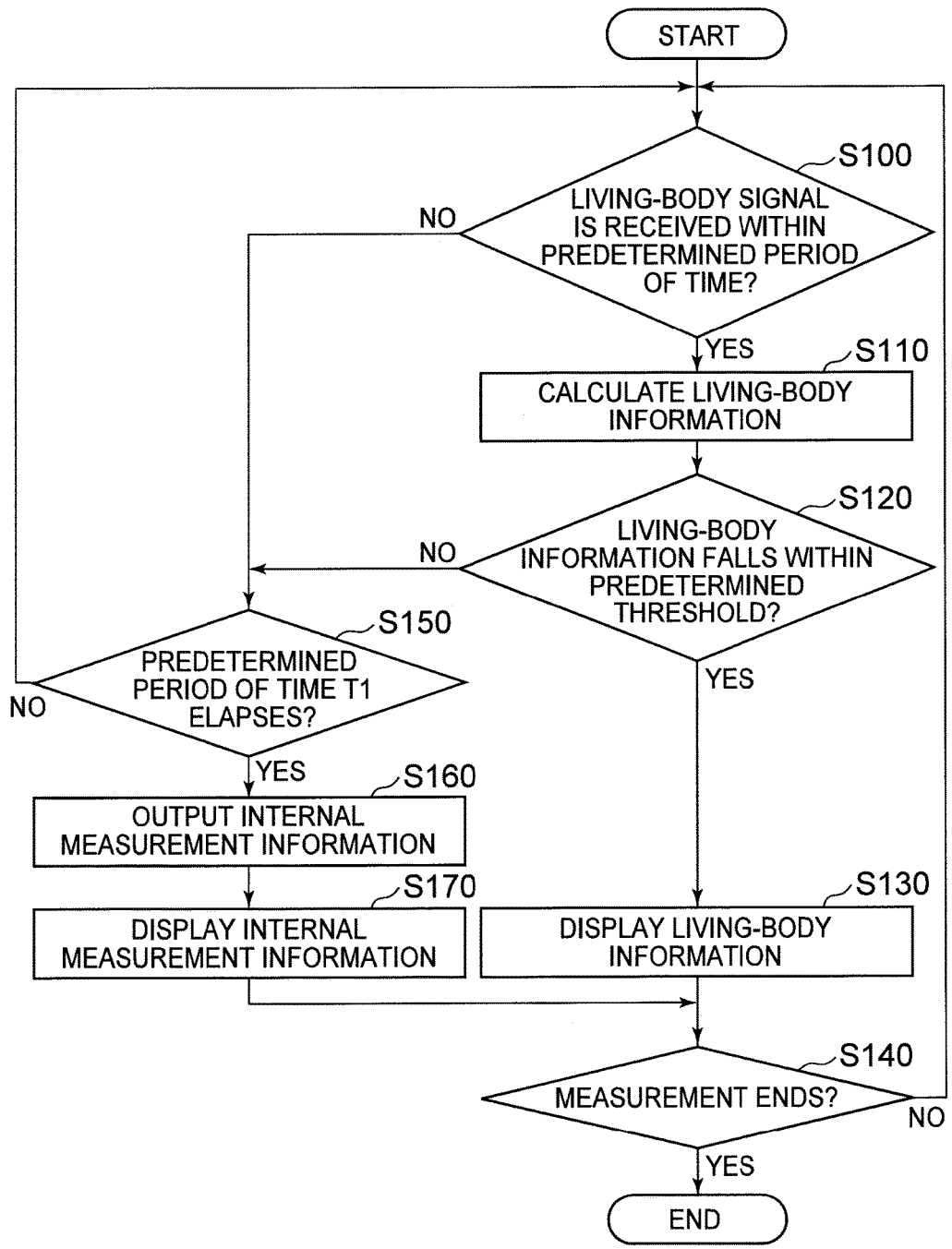
FIG. 13 is a flow chart for describing one example of an operation flow of a display information processing unit according to the second embodiment.

FIG. 13 is a flow chart for describing one example of an operation flow of the display information processing unit 220a. First, the reception determination unit 222 included in the display information processing unit 220a determines whether or not the receiving unit 210 receives the living-body signal (Step S100). If it is determined that the living-body signal is not received (Step S100—No), the reception determination unit 222 determines whether or not the predetermined period of time T1 elapses from a point in time when the calculation of the living-body information is stopped (that is, a point in time when it is determined that the living-body information is not received) (Step S150). If the reception determination unit 222 determines that the living-body signal is received (Step S100—Yes), the display information processing unit 220a calculates the living-body information, based on the received living-body signal (Step S110). Next, the display information processing unit 220a determines whether or not the living-body information calculated in Step S110 falls within a range of a predetermined threshold (Step S120). If it is determined that the living-body information does not fall within the range of the predetermined threshold (Step S120—No), the display information processing unit 220a proceeds to Step S150. If it is determined that the living-body information falls within the range of the predetermined threshold (Step S120—Yes), the display information processing unit 220a outputs the living-body information to the display control unit 230a. Then, the display control unit 230a switches to the living-body information for display on the display unit 240 (Step S130).

Next, the display information processing unit 220a determines whether or not an input from the user for ending the measurement is present (Step S140). If the input from the user for ending the measurement is not present (Step S140—No), the display information processing unit 220a returns to Step S100. If the input from the user for ending the measurement is present (Step S140—Yes), the display information processing unit 220a ends the processing.

In Step S150, if it is determined that the predetermined period of time T1 does not elapse from the point in time when the calculation of the living-body information is stopped (Step S150—No), the display information processing unit 220a returns to Step S100. In Step S150, if it is determined that the predetermined period of time T1 elapses from the point in time when the calculation of the living-body information is stopped (Step S150—Yes), the display information processing unit 220a outputs the internal measurement information (Step S160). Next, the display information processing unit 220a outputs the internal measurement information to the display control unit 230a. Then, the display control unit 230a switches to the internal measurement information for display on the display unit 240 (Step S170) and proceeds to S140.

In this manner, the running watch 200 according to the second embodiment can obtain the same effect as the running watch system 1 according to the first embodiment because the reception determination unit 222 included in the display information processing unit 220 determines whether the living-body signal is received or is not received from the chest strap 100. Furthermore, the running watch 200 displays on the display unit 240 at least one of a point in time, a time, the number of steps, steps per minute (SPM), walking Or running acceleration, a walking or running distance, energy consumed during walking or running, and so on, as the internal measurement information. Accordingly, the running watch 200 can display the multiple items of information on a size-limited region of a watch or the like, without the user operation.

Furthermore, if the reception determination unit 222 determines that the state where the living-body signal is not received is changed to the state where the living-body signal is received, the running watch 200 immediately performs the switching from the display of the internal measurement information that is displayed until just before the switching to the display of the living-body information. Accordingly, the running watch 200 can immediately notify the user that the living-body signal is received.

Furthermore, if the reception determination unit 222 determines that the state where the living-body signal is received is changed to the state where the living-body signal is not received, after the predetermined period of time T1 elapses from the time when the determination is made, the running watch 200 performs the switching from the display of the living-body information that is displayed until just before the switching to the display of the internal measurement information. Furthermore, if it is determined that the living-body information calculated by the display information processing unit 220a does not fall within the range of the predetermined threshold, after the predetermined period of time T1 elapses from the time when the determination is made, the running watch 200 performs the switching from the display of the living-body information that is displayed until just before the switching to the display of the internal measurement information. Accordingly, even though the signal received from the chest strap 100 is not stable, the running watch 200 can prevent the display from being frequently switched. Moreover, the running watch 200 can prevent the living-body signal from being continuously measured in an abnormal reception state such as when noise gets mixed in with the received living-body signal because it is determined whether or not the living-body information falls within the range of the predetermined threshold.

In addition, in order to perform the processing by each unit, a program for realizing functions of all or some of the display information processing unit 220, the display information processing unit 220a, the display control unit 230, the display control unit 230a, and the signal acquisition control unit 260 may be recorded on a computer-readable recording medium, and a computer system may be caused to read and execute the program recorded on this recording medium. In addition, the "computer system" here is defined as including an OS and hardware units such as a peripheral device.

Furthermore, if the WWW system is used, the "computer system" is defined as including an environment in which web pages are provided (or an environment in which the display is available).

Furthermore, the "computer-readable recording medium" refers to a portable medium such as a flexible disk, a magneto-optical disk, ROM, and CD-ROM, and a storage device such as a hard disk that is built into the computer system. Moreover, the "computer-readable recording medium" is defined as including whatever dynamically includes the program for a short period of time, such as a communication line that is used when transmitting the program over a network such as the Internet or over a communication circuit such as a telephone circuit and as including whatever retains the program for a constant period of time, such as volatile memory within the computer system, which functions as a server or a client in the case of including the program dynamically. Furthermore, the program may be one for realizing some of the functions described above and additionally may be one that can realize the functions described above in combination with a program that is already recorded in the computer system.

The embodiments are described above in detail referring to the drawings, but the specific configuration is not limited to the embodiments and includes an amendment to a design that falls within a scope not deviating from the gist of the present invention.

What is claimed is:

1. An electronic device comprising:
a display having first and second display portions that display information;
a living-body signal receiver that receives a living-body signal from a measurement device;
a display information processor that calculates living-body information based on the living-body signal received by the living-body signal receiver, the display information processor comprising:
an internal measurement unit that outputs a plurality of types of internal measurement information measured within the internal measurement unit; and
a determination unit that determines whether or not the living-body signal receiver receives the living-body signal; and
a display controller that, based on a result of the determination by the determination unit, performs a switching operation to switch between the internal measurement information output by the internal measurement unit and the living-body information calculated by the display information processor for display on the first and/or second display portions of the display;
wherein the display controller performs the switching operation to selectively display any one of the plurality of types of internal measurement information on each of the first and second display portions of the display when the determination unit determines that the living-body signal receiver does not receive the living-body signal;
wherein the display controller performs the switching operation to switch between display of the living-body information and any one of the plurality of types of internal measurement information on the first display portion of the display and to switch between display of the plurality of types of internal measurement information on the second display portion of the display when the determination unit determines that the living-body signal receiver receives the living-body signal; and
wherein when the determination unit determines that the living-body signal receiver receives the living-body signal, the display controller performs a control operation to control the display to continue displaying the living-body information on the first display portion of the display while the display controller performs the switching operation to switch between display of the plurality of types of internal measurement information on the second display portion of the display.

2. The electronic device according to claim 1, wherein the plurality of types of internal measurement information includes a point in time, a time, a number of steps, steps per minute, walking or running acceleration, a walking or running distance, and energy consumed during walking or running.

3. The electronic device according to claim 1, wherein the determination unit performs the determination based on whether or not the living-body signal is received within a predetermined period of time.

4. The electronic device according to claim 2, wherein the determination unit performs the determination based on whether or not the living-body signal is received within a predetermined period of time.

5. The electronic device according to claim 3, wherein if the living-body signal is received at least one time within the predetermined period of time, or if the living-body signal is continuously received within a predetermined period within the predetermined period of time, the determination unit determines that the living-body signal is received.

6. The electronic device according to claim 4, wherein if the living-body signal is received at least one time within the predetermined period of time, or if the living-body signal is continuously received within a predetermined period within the predetermined period of time, the determination unit determines that the living-body signal is received.

7. The electronic device according to claim 1, wherein the determination unit determines whether or not the living-body information calculated by the display information processor falls within a range of a predetermined threshold, and wherein the display controller performs the switching operation to switch between the internal measurement information output by the internal measurement unit and the living-body information calculated by the display information processor for display on the display based on the result of the determination by the determination unit determining whether or not the living body information falls within the range of the predetermined threshold.

8. The electronic device according to claim 2, wherein the determination unit determines whether or not the living-body information calculated by the display information processor falls within a range of a predetermined threshold, and wherein the display controller performs the switching operation to switch between the internal measurement information output by the internal measurement unit and the living-body information calculated by the display information processor for the display on the display based on the result of the determination by the determination unit determining whether or not the living body information falls within the range of the predetermined threshold.

9. The electronic device according to claim 3, wherein the determination unit determines whether or not the living-body information calculated by the display information processor falls within a range of a predetermined threshold, and wherein the display controller performs the switching operation to switch between the internal measurement information output by the internal measurement unit and the living-body information calculated by the display information processor for the display on the display based on the result of the determination by the determination unit determining whether or not the living body information falls within the range of the predetermined threshold.

10. The electronic device according to claim 4, wherein the determination unit determines whether or not the living-body information calculated by the display information processor falls within a range of a predetermined threshold, and wherein the display controller performs the switching operation to switch between the internal measurement information output by the internal measurement unit and the living-body information calculated by the display information processor for the display on the display based on the result of the determination by the determination unit determining whether or not the living body information falls within the range of the predetermined threshold.

11. The electronic device according to claim 1, further comprising: a signal acquisition controller that performs switching between settings that activate and stop the living-body signal receiver.

12. The electronic device according to claim 11, wherein the display controller causes the display to display whether the living-body signal receiver is set to be activated or is set to be stopped.

13. The electronic device according to claim 11, wherein the signal acquisition controller activates operation of the living-body signal receiver when transition to a predetermined mode is performed.

14. The electronic device according to claim 1, wherein if the determination unit determines that the living-body signal is received, the display controller performs the switching operation by switching among multiple display patterns of the display in each of which the living-body information calculated by the display information processor is displayed on the display, and wherein if the determination unit determines that the living-body signal is not received, the display controller performs the switching operation by switching among multiple display patterns of the display in each of which the internal measurement information output by the internal measurement unit is displayed on the display.

15. The electronic device according to claim 14, wherein if the determination unit determines that the living-body signal is received, the display controller immediately performs the switching operation to switch among the multiple display patterns in each of which the living-body information is displayed on the display, or if the determination unit determines that the living-body signal is received and additionally determines that the living-body information calculated by the display information processor falls within a range of a predetermined threshold, the display controller immediately performs the switching operation to switch among the multiple display patterns in each of which the living-body information is displayed on the display.

16. The electronic device according to claim 1, wherein if a state where the determination unit determines that the living-body signal is received is changed to a state where the determination unit determines that the living-body signal is not received, after waiting a predetermined period of time, the display controller performs the switching operation by switching among multiple display patterns of the display in each of which the internal measurement information measured by the internal measurement unit is displayed on the display.

17. The electronic device according to claim 1, wherein the display controller performs the switching operation to switch between the internal measurement information and the living-body information so as to be displayed by the display in a display pattern that differs from one mode to another, and in a predetermined mode, the display controller performs the switching operation to switch between the internal measurement information and the living-body information.

18. An electronic device comprising:
a living-body signal receiver that receives a living-body signal;
a display information processor that calculates living-body information based on a living-body signal received by the living-body signal receiver, that measures and outputs a plurality of types of internal measurement information, and that determines whether or not the living-body signal receiver receives the living-body signal;
a display having first and second display portions configured to display the living-body information and the internal measurement information; and
a display controller that performs a switching operation to switch between the living-body information and the internal measurement information for display on the first and/or second display portions of the display based on the result of the determination by the display information processor;
wherein the display controller performs the switching operation to selectively display any one of the plurality of types of internal measurement information on each of the first and second display portions of the display when the display information processor determines that the living-body signal receiver does not receive the living-body signal;
wherein the display controller performs the switching operation to switch between display of the living-body information and any one of the plurality of types of internal measurement information on the first display portion of the display and to switch between display of the plurality of types of internal measurement information on the second display portion of the display when the display information processor determines that the living-body signal receiver receives the living-body signal; and
wherein when the display information processor determines that the living-body signal receiver receives the living-body signal, the display controller performs a control operation to control the display to continue displaying the living-body information on the first display portion of the display while the display controller performs the switching operation to switch between display of the plurality of types of internal measurement information on the second display portion of the display.

19. An electronic device comprising:
a living-body signal receiver that receives a living-body signal;
a display information processor that determines whether or not the living-body signal receiver receives the living-body signal and calculates living-body information based on a living-body signal received by the living-body signal receiver, the display information processor including an internal measurement unit that measures and outputs internal measurement information;
a display configured to display the living-body information and the internal measurement information; and
a display controller that performs a switching operation to switch between the living-body information and the internal measurement information for display on the display based on the result of the determination by the display information processor, and that performs a controlling operation to cause the display to continue displaying the living-body information each time the display information processor determines that the living-body signal receiver receives the living-body signal;
wherein the display comprises a display screen having two display portions;
wherein when the display information processor determines that the living-body signal receiver does not receive the living-body signal, the display controller performs the switching operation for display of the internal measurement information, but not the living-body information, on the two display portions of the display screen; and
wherein when the display information processor determines that the living-body signal receiver receives the living-body signal, the display controller performs the switching operation to switch the display on one of the two display portions of the display from the internal measurement information to the living body information while the other of the two display portions of the display continues to display the internal measurement information.

* * * * *